(12) United States Patent
Gardiner et al.

(10) Patent No.: US 7,476,405 B2
(45) Date of Patent: Jan. 13, 2009

(54) COMPOSITIONS AND METHODS FOR THE INDUCTION AND MAINTENANCE OF QUALITY SLEEP

(75) Inventors: Paul T. Gardiner, Mississauga (CA); Marvin A. Heuer, Mississauga (CA); Shan Chaudhuri, Mississauga (CA); Kenneth Clement, Mississauge (CA)

(73) Assignee: Iomedix Sleep International SRL, Ontario (CA)

( * ) Notice: Subject to any disclaimer, the term of this patent is extended or adjusted under 35 U.S.C. 154(b) by 0 days.

(21) Appl. No.: 11/486,866

(22) Filed: Jul. 14, 2006

(65) Prior Publication Data

US 2007/0196348 A1    Aug. 23, 2007

Related U.S. Application Data

(60) Provisional application No. 60/776,325, filed on Feb. 23, 2006.

(51) Int. Cl.
*A01N 65/00* (2006.01)
*A61K 36/00* (2006.01)

(52) U.S. Cl. .................. 424/725; 424/773; 424/775; 424/778

(58) Field of Classification Search .............. None
See application file for complete search history.

(56) References Cited

U.S. PATENT DOCUMENTS

| 5,641,801 | A | 6/1997 | Wurtman |
| 5,681,578 | A | 10/1997 | Sahley |
| 5,716,978 | A | 2/1998 | Lewy |
| 6,080,410 | A | 6/2000 | Bewicke |
| 6,277,396 | B1 * | 8/2001 | Dente ........................ 424/439 |
| 6,312,736 | B1 | 11/2001 | Kelly et al. |
| 6,383,527 | B1 | 5/2002 | Artman et al. |
| 6,703,412 | B1 | 3/2004 | Rosenthal |
| 6,770,263 | B1 | 8/2004 | Brucker |
| 6,869,622 | B2 | 3/2005 | Andrews et al. |
| 7,045,158 | B2 | 5/2006 | Wolfson et al. |
| 2001/0011083 | A1 * | 8/2001 | Barr et al. .................. 514/159 |
| 2002/0127285 | A1 * | 9/2002 | Xiu ............................ 424/725 |
| 2003/0013639 | A1 * | 1/2003 | Yurchak et al. ................ 514/2 |
| 2003/0232091 | A1 * | 12/2003 | Shefer et al. ................ 424/490 |
| 2004/0063661 | A1 * | 4/2004 | Linnane ........................ 514/50 |
| 2005/0129783 | A1 * | 6/2005 | McCleary et al. ........... 424/646 |
| 2005/0244517 | A1 * | 11/2005 | Hall et al. ................... 424/733 |
| 2005/0272690 | A1 * | 12/2005 | Cremisi ....................... 514/52 |

FOREIGN PATENT DOCUMENTS

HU    62477    *  5/1993

OTHER PUBLICATIONS

Abourashed EA, Koetter U, Brattstrom A. In vitro binding experiments with a Valerian, hops and their fixed combination extract (Ze91019) to selected central nervous system receptors. Phytomedicine. Nov. 2004;11(7-8):633-8.).
Akhondzadeh et al, Melissa officinalis extract in the treatment of patients with mild to moderate Alzheimer's disease: a double blind, randomised, placebo controlled trial. J Neurol Neurosurg Psychiatry. Jul. 2003;74(7):863-6.
Akhondzadeh et al., Comparison of Lavandula angustifolia Mill. tincture and imipramine in the treatment of mild to moderate depression: a double-blind, randomized trial. Prog Neuropsychopharmacol Biol Psychiatry. Feb. 2003;27(1):123-7.
Akhondzadeh et al., Passionflower in the treatment of generalized anxiety: a pilot double-blind randomized controlled trial with oxazepam. J Clin Pharm Ther. Oct. 2001;26(5):363-7.
Andrade R. of membrane excitability in the central nervous system by serotonin receptor subtypes. Ann N Y Acad Sci. Dec. 15, 1998;861:190-203.
Aoshima et al., Effects of beer and hop on ionotropic gamma-aminobutyric acid receptors. J Agric Food Chem. Apr. 5, 2006;54(7):2514-9.).
Arangino et al., Effects of melatonin on vascular reactivity, catecholamine levels, and blood pressure in healthy men. Am J Cardiol. May 1, 1999;83(9):1417-9.
Avery et al., Guidelines for prescribing melatonin. Ann Med. Feb. 1998;30(1):122-30.
Awad et at., Phytochemical and biological analysis of skullcap (*Scutellaria lateriflora* L.): a medicinal plant with anxiolytic properties. Phytomedicine. Nov. 2003;10(8):640-9.

(Continued)

*Primary Examiner*—Michael Meller
*Assistant Examiner*—Qiuwen Mi
(74) *Attorney, Agent, or Firm*—Fitzpatrick, Cella, Harper & Scinto

(57) ABSTRACT

Supplemental compositions, and methods for administering same to a user, are provided for promoting a restful night's sleep by speedily inducing a person to fall asleep and to maintain sleep, as well as alleviating minor aches and pains so as to further improve the quality of a person sleep. The supplemental composition may include at least an extract of Valerian Root, an extract of Willow Bark and Melatonin or a derivative thereof. The supplemental composition may be provided for consumption at least one time daily, e.g., prior to sleep.

6 Claims, No Drawings

OTHER PUBLICATIONS

Brzezinski et al., Effects of exogenous melatonin on sleep: a meta-analysis. Sleep Med Rev. Feb. 2005;9(1):41-50.

Buscemi et al., The efficacy and safety of exogenous melatonin for primary sleep disorders. A meta-analysis. J Gen Intern Med. Dec. 2005;20(12):1151-8.

Chrubasik et al., Treatment of low back pain exacerbations with willow bark extract: a randomized double-blind study. Am J Med. Jul. 2000;109(1):9-14.

Dietz et al., Valerian extract and valerenic acid are partial agonists of the 5-HT5a receptor in vitro. Brain Res Mol Brain Res. Aug. 18, 2005;138(2):191-7.

Dietz et al., Xanthohumol isolated from *Humulus lupulus* Inhibits menadione-induced DNA damage through induction of quinone reductase. Chem Res Toxicol. Aug. 2005;18(8):1296-305.

Dijk et al., Integration of human sleep-wake regulation and circadian rhythmicity. J Appl Physiol. Feb. 2002; 92(2):852-62.

Dimpfel et al,. Effects of lozenge containing lavender oil, extracts from hops, lemon balm and oat on electrical brain activity of volunteers. Eur J Med Res. Sep. 29, 2004;9(9):423-31.

Dubocovich et al., Functional MT1 and MT2 melatonin receptors in mammals. Endocrine. Jul. 2005;27(2):101-10.

Everson CA. Sustained sleep deprivation impairs host defense. Am J Physiol. Nov. 1993;265(5 Pt 2):R1148-54.

Feng et al. . Serotonin receptors modulate GABA(A) receptor channels through activation of anchored protein kinase C in prefrontal cortical neurons. J Neurosci. Sep. 1, 2001;21(17):6502-11.

Francis et al., Effect of valerian, Valeriana edulis, on sleep difficulties in children with intellectual deficits: randomised trial. Phytomedicine. May 2002;9(4):273-9.

Fussel et al., Effects of a fixed valerian-Hop extract combination (Ze 91019) on sleep polygraphy in patients with non-organic insomnia: a pilot study. Eur J Med Res. Sep. 18, 2000;5(9):385-90.

Gafner et al. Inhibition of [3H]-LSD binding to 5-HT7 receptors by flavonoids from *Scutellaria lateriflora*. J Nat Prod. Apr. 2003;66(4):535-7.

Gais et al., Early sleep triggers memory for early visual discrimination skills. Nat Neurosci. Dec. 2000;2(12):1335-9.

Gottlieb et al., Association of sleep time with diabetes mellitus and impaired glucose tolerance. Arch Intern Med. Apr. 25, 2005;165(8):863-7.

Gyllenhaal et al., Efficacy and safety of herbal stimulants and sedatives in sleep disorders. Sleep Med Rev. Jun. 2000;4(3):229-251.

Hastings MH. Central clocking. Trends Neurosci. Oct. 1997;20(10):459-64.

Hohmann et al., Protective effects of the aerial parts of *Salvia officinalis, Melissa Officinalis* and *Lavandula angustifolia* and their constituents against enzyme-dependent and enzyme-independent lipid peroxidation. Planta Med. Aug. 1999;65(6):576-8.

Holmes et al., Lavender oil as a treatment for agitated behaviour in severe dementia: a placebo controlled study. Int J Geriatr Psychiatry. Apr. 2002;17(4):305-8.

Hughes et al., The role of melatonin and circadian phase in age-related sleep-maintenance insomnia: assessment in a clinical trial of melatonin replacement. Sleep. 1998;21(1):52-68.

Imagawa et al., Coenzyme Q10, iron, and vitamin B6 in genetically-confirmed Alzheimer's disease. Lancet. Sep. 12, 1992;340(8820):671.

Irwin et al., Partial night sleep deprivation reduces natural killer and cellular immune responses in humans. FASEB J. Apr. 1996;10(5):643-53.

Kamikawa et al., Effects of coenzyme Q10 on exercise tolerance in chronic stable *angina pectoris*. Am J Cardiol. Aug. 1, 1985;56(4):247-51.

Kayumov et al., A randomized, double-blind, placebo-controlled crossover study of the effect of exogenous melatonin on delayed sleep phase syndrome. Psychosom Med. Jan.-Feb. 2001;63(1):40-8.

Kennedy et al. Modulation of mood and cognitive performance following acute administration of *Melissa officinalis* (lemon balm). Pharmacol Biochem Behav. Jul. 2002;72(4):953-64.

Kennedy et al., Anxiolytic effects of a combination of *Melissa officinalis* and *Valeriana officinalis* during laboratory induced stress. Phytother Res. Feb. 2006;20(2):96-102.

Kennedy et al., Modulation of mood and cognitive performance following acute administration of single doses of *Melissa officinalis* (Lemon balm) with human CNS nicotinic and muscarinic receptor-binding properties. Neuropsychopharmacology. Oct. 2003;28(10):1871-81.

Kennedy et al.,. Attenuation of laboratory-induced stress in humans after acute administration of *Melissa officinalis* (Lemon Balm). Psychosom Med. Jul.-Aug. 2004;66(4):607-13.

Kunz et al., Melatonin in patients with reduced REM sleep duration: two randomized controlled trials. J Clin Endocrinol Metab. Jan. 2004;89(1):128-34.

Langsjoen et al., Treatment of essential hypertension with coenzyme Q10. Mol Aspects Med. 1994;15 Suppl:S265-72.

Leathwood et al., Aqueous extract of valerian root (*Valeriana officinalis L.*) improves sleep quality in man. Pharmacol Biochem Behav. Jul. 1982;17(1):65-71.

Lindahl et al., Double blind study of a valerian preparation. Pharmacol Biochem Behav. Apr. 1989;32(4):1065-6.

Lis-Balchin et al., Studies on the mode of action of the essential oil of lavender (*Lavandula angustifolia* P. Miller). Phytother Res. Sep. 1999;13(6):540-2.

Matsumoto M. The hypnotic effects of melatonin treatment on diurnal sleep in humans. Psychiatry Clin Neurosci. Apr. 1999;53(2):243-5.

Mendelson WB. Sleep-inducing effects of adenosine microinjections into the medial preoptic area are blocked by flumazenil. Brain Res. Jan. 10, 2000;852(2):479-81.

Menghini et al, TLC determination of flavonoid accumulation in clonal populations of *Passiflora incarnata* L. Pharmacol Res Commun. Dec. 1988;20 Suppl 5:113-6.

Mortensen SA. Perspectives on therapy of cardiovascular diseases with coenzyme Q10 (ubiquinone). Clin Investig. 1993;71(8 Suppl):S116-23.

Muller CE, Schumacher B, Brattstrom A, Abourashed EA, Koetter U. Interactions of valerian extracts and a fixed valerian-hop extract combination with adenosine receptors. Life Sci. Sep. 6, 2002;71(16):1939-49.

Mundey et al., Phase-dependent treatment of delayed sleep phase syndrome with melatonin. Sleep. Oct. 1, 2005;28(10):1271-8.

Nagtegaal et al., Delayed sleep phase syndrome: A placebo-controlled cross-over study on the effects of melatonin administered five hours before the individual dim light melatonin onset. J Sleep Res. Jun. 1998;7(2):135-43.

Ninomiya et al., Effects of exogenous melatonin on pituitary hormones in humans. Clin Physiol. May 2001;21(3):292-9.

Olsen et al., Molecular biology of GABAA receptors. FASEB J. 19 Valenstein M, Taylor KK, Austin K, Kales HC, McCarthy JF, Blow FC. Benzodiazepine use among depressed patients treated in mental health settings. Am J Psychiatry. Apr. 2004;161(4):654-61.).90 Mar;4(5):1469-80).

Pereira et al., A HPTLC densitometric determination of flavonoids from *Passiflora alata, P. edulis, P. incarnata* and *P. caerulea* and comparison with HPLC method. Phytochem Anal. Jul.-Aug. 2004;15(4):241-8.

Portas et al., On-line detection of extracellular levels of serotonin in dorsal raphe nucleus and frontal cortex over the sleep/wake cycle in the freely moving rat. Neuroscience. Apr. 1998;83(3):807-1.

Reiter RJ. melatonin: cell biology of its synthesis and of its physiological interactions. Endocr Rev. May 1991;12(2):151-80.

Roth et al., Daytime consequences and correlates of insomnia in the United States: results of the 1991 National Sleep Foundation Survey. II. Sleep. May 1, 1999;22 Suppl 2:S354-8.

Sandor et al., J. Efficacy of coenzyme Q10 in migraine prophylaxis: a randomized controlled trial. Neurology. Feb. 22, 2005;64(4):713-5.

Sawynok J. Pharmacological rationale for the clinical use of caffeine. Drugs. Jan. 1995;49(1):37-50.

Schmid et al., Efficacy and tolerability of a standardized willow bark extract in patients with osteoarthritis: randomized placebo-controlled, double blind clinical trial. Phytother Res. Jun. 2001;15(4):344-50.

Shults et al., Coenzyme Q10 levels correlate with the activities of complexes I and II/III in mitochondria from parkinsonian and nonparkinsonian subjects. Ann Neurol. Aug. 1997;42(2):261-4.

Shults et al., Parkinson Study Group. Effects of coenzyme Q10 in early Parkinson disease: evidence of slowing of the functional decline. Arch Neurol. Oct. 2002;59(10):1541-50.

Soja AM, Mortensen SA. Treatment of congestive heart failure with coenzyme Q10 illuminated by meta-analyses of clinical trials. Mol Aspects Med. 1997;18 Suppl:S159-68.

Soulimani et al., Behavioural effects of Passiflora incarnata L. and its indole alkaloid and flavonoid derivatives and maltol in the mouse. J Ethnopharmacol. Jun. 1997;57(1):11-20.

Stickgold et al., Visual discrimination learning requires sleep after training. Nat Neurosci. Dec. 2000;3(12):1237-8.

Stoller MK. Economic effects of insomnia. Clin Ther. Sep.-Oct. 1994;16(5):873-97.

Strecker et al., Adenosinergic modulation of basal forebrain and basal forebrain and preoptic/anterior hypothalamic neuronal activity in the control of behavioral state. Behav Brain Res. Nov. 2000;115(2):183-204.

Takasaki et al., An Analysis of Effectiveness of Activated Co-enzyme Q10 on Subjects by Using Acoustic Technology. Biopharma Ltd. Tokyo Japan.

Thakkar et al., A1 receptor and adenosinergic homeostatic regulation of sleep-wakefulness: effects of antisense to the A1 receptor in the cholinergic basal forebrain. J Neurosci. May 15, 2003;23(10):4278-87.

Thomas et al., Inhibition of LDL oxidation by ubiquinol-10. A protective mechanism for coenzyme Q in atherogenesis? Mol Aspects Med. 1997;18 Suppl:S85-103.

Valenstein et al. , Benzodiazepine use among depressed patients treated in mental health settings. Am J Psychiatry. Apr. 2004;161(4):654-61.

Wake et al., E. acetylcholine receptor activity in European medicinal plants traditionally used to improve failing memory. J Ethnopharmacol. Feb. 2000;69(2):105-14.

Weber et al., Antioxidative effect of dietary coenzyme Q10 in human blood plasma.. Int J Vitam Nutr Res. 1994;64(4):311-5.

Wolfman et al., Possible anxiolytic effects of chrysin, a central benzodiazepine receptor ligand isolated from Passiflora coerulea. Pharmacol Biochem Behav. Jan. 1994;47(1):1-4.

Wolfson et al., An investigation into the efficacy of Scutellaria lateriflora in healthy volunteers. Altern Ther Health Med. Mar.-Apr. 2003;9(2):74-8.

Wyatt et al., . Circadian temperature and melatonin rhythms, sleep, and neurobehavioral function in humans living on a 20-h day. Am J Physiol. Oct. 1999;277(4 Pt 2):R1152-63.

Zammit et al., Quality of life in people with insomnia. Sleep. May 1, 1999;22 Suppl 2:S379-85.

Zanoli P, Rivasi M, Zavatti M, Brusiani F, Baraldi M. New insight in the neuropharmacological activity of Humulus lupulus L. J Ethnopharmacol. Oct. 31, 2005;102-6.

Zeitzer et al., Extracellular adenosine in the human brain sleep and sleep deprivation: an in vivo microdialysis study. Sleep. Apr. 1, 2006;29(4):455-61.

Zhdanova et al., Melatonin treatment for age-related insomnia. J Clin Endocrinol Metab. Oct. 2001;86(10):4727-30.

Zhdanova et al., Sleep-inducing effects of low doses of melatonin ingested in the evening. Clin Pharmacol Ther. May 1995;57(5):552-8.

* cited by examiner

COMPOSITIONS AND METHODS FOR THE INDUCTION AND MAINTENANCE OF QUALITY SLEEP

RELATED APPLICATIONS

This application is related to and claims benefit of priority to Applicant's U.S. Provisional Patent Application Ser. No. 60/776,325 entitled "Compositions and Methods for Increasing Bioavailability of Compositions for Performance Improvement", filed Feb. 23, 2006, the disclosure of which is hereby fully incorporated by reference.

FIELD OF THE INVENTION

The present invention relates to a composition to aid in the induction and maintenance of sleep in a user, e.g., human.

BACKGROUND OF THE INVENTION

Sleep typically occupies about one-third of a person's life and affects a person's mental and physical well being. It additionally affects mood, behavior and physiology. Sleep and the control of sleep is a complex process involving multiple chemicals and brain structures. It is a dynamic process involving distinct physiological changes and involves both positive and negative signaling. The regulation of sleep in humans is governed by three processes—each influenced by hormonal and environmental factors: a daily sleep-wake cycle influenced by a circadian rhythm (24 hour cycle) tied to light-dark cycles controlled by a cluster of about 10,000 neurons located in the hypothalamus behind the eyes, called the suprachiasmatic nuclei (Hastings M H. Central clocking. Trends Neurosci. 1997 October; 20(10):459-64.); a separable oscillating sleep homeostatic process influenced by prior sleep (Dijk D J, Lockley S W. Integration of human sleep-wake regulation and circadian rhythmicity. J Appl Physiol. 2002 February; 92(2):852-62.); and an ultradian rhythm which occurs within the 24 hour circadian cycle.

The need for sleep is a biological drive similar to thirst or hunger. Interestingly though, the function of sleep is largely unknown, however some evidence indicates that sleep is required for learning (Stickgold R, James L, Hobson J A. Visual discrimination learning requires sleep after training. Nat Neurosci. 2000 December; 3(12):1237-8; Gais S, Plihal W, Wagner U, Born J. Early sleep triggers memory for early visual discrimination skills. Nat Neurosci. 2000 December; 3(12):1335-9.). Additionally, sleep deprivation studies in rats have shown that when rats are not allowed to sleep, the end-result is death apparently related to immune system failure (Everson C A. Sustained sleep deprivation impairs host defense. Am J Physiol. 1993 November; 265(5 Pt 2):R1148-54.). In humans, similarly, mild sleep deprivation also results in indications of impaired immune system function (Irwin M, McClintick J, Costlow C, Fortner M, White J, Gillin J C. Partial night sleep deprivation reduces natural killer and cellular immune responses in humans. FASEB J. 1996 April; 10(5):643-53.). Although specific sleep requirements vary from individual to individual, sleeping less than six hours per day has been shown to increase the risk of glucose intolerance and diabetes (Gottlieb D J, Punjabi N M, Newman A B, Resnick H E, Redline S, Baldwin C M, Nieto F J. Association of sleep time with diabetes mellitus and impaired glucose tolerance. Arch Intern Med. 2005 Apr. 25; 165(8):863-7.). Insomnia has been estimated to affect 40% of North Americans per year (Stoller M K. Economic effects of insomnia. Clin Ther. 1994 September-October; 16(5):873-97). A study by the U.S. National Sleep Foundation and the Gallup Organization involving 1,000 randomly selected Americans revealed that insomnia negatively impacts activities during waking function and effects quality of life (Roth T, Ancoli-Israel S. Daytime consequences and correlates of insomnia in the United States: results of the 1991 National Sleep Foundation Survey. II. Sleep. 1999 May 1; 22 Suppl 2:S354-8.). Another study involving 261 insomnia sufferers and 101 individuals with no sleep complaints revealed that insomnia significantly impairs quality of life (Zammit G K, Weiner J, Damato N, Sillup G P, McMillan C A. Quality of life in people with insomnia. Sleep. 1999 May 1; 22 Suppl 2:S379-85.).

The neurotransmitter Gamma Aminobutyric Acid (GABA) is a primary inhibitory neurotransmitter. One of its effects is to induce sleep. The GABA-receptors are associated with chloride ion channels—signaling through the GABA-receptor changes the electrochemical gradient of the neuron, leading to activity inhibition (Olsen R W, Tobin A J. Molecular biology of GABAA receptors. FASEB J. 1990 March; 4(5): 1469-80). Benzodiazepines are thought to act via interaction with the GABA receptor; enhancing the inhibitory effects of GABA. As such, Benzodiazepines are a widely used class of drugs primarily used as tranquilizers, muscle-relaxants, hypnotics or sedatives (Valenstein M, Taylor K K, Austin K, Kales H C, McCarthy J F, Blow F C. Benzodiazepine use among depressed patients treated in mental health settings. Am J Psychiatry. 2004 April; 161(4):654-61.). Additionally, Adenosine, a neuromodulator, may induce sleep by extracellular accumulation in specific brain regions such as the basal forebrain during prolonged wakefulness (Strecker R E, Morairty S, Thakkar M M, Porkka-Heiskanen T, Basheer R, Dauphin L J, Rainnie D G, Portas C M, Greene R W, McCarley R W. Adenosinergic modulation of basal forebrain and preoptic/anterior hypothalamic neuronal activity in the control of behavioral state. Behav Brain Res. 2000 November; 115(2):183-204; Zeitzer J M, Morales-Villagran A, Maidment N T, Behnke E J, Ackerson L C, Lopez-Rodriguez F, Fried I, Engel J Jr, Wilson C L. Extracellular adenosine in the human brain during sleep and sleep deprivation: an in vivo microdialysis study. Sleep. 2006 Apr. 1; 29(4):455-61.). Actions on both the GABA-benzodiazepine receptor complex (Mendelson W B. Sleep-inducing effects of adenosine microinjections into the medial preoptic area are blocked by flumazenil. Brain Res. 2000 Jan. 10; 852(2):479-81.) and/or the adenosine A1 receptor (Thakkar M M, Winston S, McCarley R W. A1 receptor and adenosinergic homeostatic regulation of sleep-wakefulness: effects of antisense to the A1 receptor in the cholinergic basal forebrain. J Neurosci. 2003 May 15; 23(10):4278-87.) can lead to the induction and maintenance of sleep. The stimulatory effects of caffeine are thought to be due to antagonism of adenosine A1 receptors (Sawynok J. Pharmacological rationale for the clinical use of caffeine. Drugs. 1995 January; 49(1):37-50.), wherein an aroused state is observed.

Another chemical associated with sleep is Melatonin. It is a hormone produced by the pineal gland from the amino acid tryptophan. Production is rhythmic in keeping with an intrinsic cycle of approximately 24-hours in duration, wherein levels are low during the day and increasing towards the nighttime (Wyatt J K, Ritz-De Cecco A, Czeisler C A, Dijk D J. Circadian temperature and melatonin rhythms, sleep, and neurobehavioral function in humans living on a 20-h day. Am J Physiol. 1999 October; 277(4 Pt 2):R1152-63). Melatonin appears to have two distinct effects on the circadian clock: neuronal inhibition and phase-shifting of the sleep cycle (Liu C, Weaver D R, Jin X, Shearman L P, Pieschl R L, Gribkoff V K, Reppert S M. Molecular dissection of two distinct actions of melatonin on the suprachiasmatic circadian clock. Neuron. 1997 July; 19(1):91-102.). Oral administration of supplemental melatonin during the day induces sleepiness and improves night sleep (Dollins A B, Zhdanova I V, Wurtman R J, Lynch H J, Deng M H. Effect of inducing nocturnal serum melatonin concentrations in daytime on sleep, mood, body temperature, and performance. Proc Natl Acad Sci USA. 1994 Mar. 1; 91(5):1824-8.). Two types of melatonin G-protein coupled receptors have been classified in mammals and termed MT1 and MT2 (Dubocovich M L, Markowska M. Functional MT1 and MT2 melatonin receptors in mammals. Endocrine. 2005 July; 27(2): 101-10.).

Serotonin (5-hydroxytryptamine, 5HT), like melatonin, also displays a diurnal pattern; however, it functions in an opposing rhythm with daytime levels being higher than nighttime levels Portas C M, Bjorvatn B, Fagerland S, Gronli J, Mundal V, Sorensen E, Ursin R. On-line detection of extracellular levels of serotonin in dorsal raphe nucleus and frontal cortex over the sleep/wake cycle in the freely moving rat. Neuroscience. 1998 April; 83(3):807-1.). Three basic serotonin receptor types have been identified: 5HT-1, 5HT-2 and 5HT-3. Several subtypes of 5HT-1 have also been identified. The exact response of cells to serotonin depends on the receptor types expressed (Andrade R. of membrane excitability in the central nervous system by serotonin receptor subtypes. Ann N Y Acad Sci. 1998 Dec. 15; 861:190-203.) however, Serotonin has been shown to inhibit GABA receptors (Feng J, Cai X, Zhao J, Yan Z. Serotonin receptors modulate GABA (A) receptor channels through activation of anchored protein kinase C in prefrontal cortical neurons. J Neurosci. 2001 Sep. 1; 21(17):6502-11.), likely contributing to the opposing actions of serotonin and GABA and play a role in sleep.

SUMMARY OF THE INVENTION

The present invention according to one embodiment thereof, provides for a composition directed towards the induction of sleep. More specifically, the invention is directed towards a sleep-promoting and pain-relief composition. Advantageously, the sleep-promoting and pain-relief composition of the present invention may additionally provide for maintenance of sleep, thereby promoting a good quality, restful sleep as well as alleviating minor aches and pains, thus further improving the quality of the person's sleep. The composition of the present invention comprises an extract of Valerian Root, an extract of Willow Bark and Melatonin or a derivative thereof. For example, the present invention may be effective in promoting a restful night's sleep by speedily inducing a person to fall asleep and maintain sleep as well as alleviating minor aches and pains further improving the quality of an individual's, e.g. a human or animal, sleep. Furthermore, the present invention advantageously provides a method for the maintenance of sleep thereby promoting a good quality, restful sleep as well as alleviating minor aches and pains, thus further improving the quality of an individual's, e.g. human or animal, sleep by administering to a human or a animal a composition comprising an extract of Valerian Root, an extract of Willow Bark and Melatonin or a derivative thereof.

According to an embodiment, the present invention may provide a composition comprising an extract of Valerian Root, an extract of Willow Bark and Melatonin or a derivative thereof. Additionally, the composition may include one or more of an extract of Hops cone, Lavender flower powder, an extract of Passionflower, Skullcap powder, an extract of Coenzyme Q10, a leaf of extract Lemon Balm. The composition may include a time-release mechanism, e.g., wherein the time-release mechanism provides 4 hours of active compound release. Also, the melatonin may be incorporated into a tablet coating to promote sleep more quickly, e.g., to promote instant or immediate sleep. Also, in an embodiment of the present invention, all or a portion of the melatonin may be fine-milled. Advantageously, the extract of Valerian Root, the extract of Willow Bark and the Melatonin or a derivative thereof, are provided in amounts effective to at least one of promote sleep and relieve pain.

DETAILED DESCRIPTION OF THE INVENTION

The present invention according to an embodiment thereof is advantageously directed towards a sleep-promoting and pain-relief composition which, for example, may induce sleep and promote the maintenance of sleep leading to a restful night's sleep, as well as alleviate minor aches and pains, further improving the quality of a person's sleep. Compounds employed in various embodiments of the present invention have been shown to be active at receptor sites in the central nervous system that relate to the induction and maintenance of sleep. Moreover, the composition of the present invention also contains compounds shown to alleviate minor aches and pains.

In an embodiment, the present invention may include the use of combinations, wherein the combination includes, without being limited to, one or more of the following: Melatonin, Coenzyme Q10, Lemon Balm leaf extract, Hops cone extract, Lavender flower extract, Passionflower extract, Skullcap, deodorized Valerian root and Willow bark extract. The supplement may be consumed in any form, e.g., a capsule, a tablet, a caplet, a liquid beverage, a powder beverage mix, or as a dietary gel. The preferred dosage form of the present embodiment is a timed release caplet.

As set forth above, the dosage form of the diet supplement, in accordance with the example embodiment set forth below, may be provided in accordance with customary processing techniques for herbal and/or dietary supplements, wherein the active ingredients are suitably processed into a desired form. In accordance with an embodiment of the present invention, one or more ingredients of the diet supplement are processed so as to form fine-milled particles. For instance, in an embodiment, one or more ingredients of the supplemental dietary composition is processed by a large-scale dry milling technique that produces fine particles, preferably known as fine-milled particles. The use of dry milling techniques, in combination with excipients and polymers, to form fine-milled particles has been shown to improve flow and dispersability, stability, resistance to moisture, bioavailability, and dissolution/release properties. Formulations may benefit by containing fine-milled particles because providing one or more ingredients in fine-milled particle sizes may optimize one or more of the flow and dispersability, stability, resistance to moisture, bioavailability, and dissolution/release properties of the one or more ingredients in a diet supplement. In vitro tests designed to simulate the environment of a stomach were performed to test the dissolution rate of fine-milled particle tablets relative to tablets having particles that are not fine-milled. These test showed that in tablets produced from fine-milled particles the time to 100% dissolution was approximately 15 minutes. In the case of non-fine-milled particle compositions, only 90% dissolution was observed after 120 minutes. In a preferred embodiment, the supplemental composition contains fine-milled particles having an average size between about 2 nm and about 50 nm.

U.S. Provisional Patent Application 60/776,325 discloses a method for improving the absorption, palatability, taste, texture, and bioavailability of compounds by increasing the solubility of compounds in proprietary formulations for the purposes of enhancing or improving muscle size, growth and/or recovery time and/or weight loss. The increased bioavailability of the compound or ingredients is achieved by reducing the particle size via "fine-milling" thereby increasing the surface area-to-volume ratio of each particle, thus increasing the rate of dissolution. The compositions and methods disclosed promote increased bioavailability by increasing the total surface area of poorly soluble particles, thereby increasing the rate of absorption.

As used herein the, term "fine-milled" and/or "fine-milling" refers to the process of micronization. Micronization is a mechanical process that involves the application of force to a particle, thereby resulting in a reduction in the size of the particle. The force, in the case of micronization, may be applied in any manner such as, e.g., the collision of particles at high rates of speed, grinding, or by an air-jet micronizer. In a preferred embodiment, fine-milled particles are obtained by jet-milling with nitrogen and compressed air.

As used herein, the term "particle size" refers to the diameter of the particle. The term "average particle size" means that at least 50% of the particles in a sample will have the specified particle size. Preferably, at least 80% of the particles in a sample will have the specified particle size, and more preferably, at least 90% of the particles in a given sample will have the specified particle size.

The size of a particle can be determined by any of the methods known within the art. Methods for particle size determination which may be employed are, e.g., sieves, sedimentation, electrozone sensing (Coulter counter), microscopy, and/or Low Angle Laser Light Scattering. The preferred methods for the particle size determination of the present invention are the methods which are most commonly used in the pharmaceutical industry, such as laser diffraction, e.g., via light scattering Coulter Delsa 440SX.

The fine-milling process may be employed in the processing of one or more of the ingredients of the present invention in the dosage forms of tablets (e.g., immediate-release film coated, modified-release and fast-dissolving), capsules (e.g., immediate-release and modified-release), liquid dispersions, powders, drink mixes, etc.

Furthermore, the dosage form of the nutritional supplement in accordance with the aforementioned embodiment or further embodiments as interpreted by one of skill in the art related to the present invention may be provided in accordance with customary processing techniques for herbal and/or dietary and/or nutritional supplements in any of the forms mentioned above.

Melatonin

Melatonin is a hormone produced by the pineal gland from tryptophan and is involved in sleep regulation (Reiter R J. melatonin: cell biology of its synthesis and of its physiological interactions. Endocr Rev. 1991 May; 12(2):151-80.). It is used to treat sleep disorders such as insomnia and 'jet lag' by stimulating the release of specific pituitary hormones (Ninomiya T, Iwatani N, Tomoda A, Miike T. Effects of exogenous melatonin on pituitary hormones in humans. Clin Physiol. 2001 May; 21(3):292-9.) and adjusting the circadian rhythm to coincide with the local day and nighttime.

Melatonin supplementation has been demonstrated to be safe and effective at increasing the total amount of sleep time in healthy subjects (Matsumoto M. The hypnotic effects of melatonin treatment on diurnal sleep in humans. Psychiatry Clin Neurosci. 1999 April; 53(2):243-5.). Moreover, Melatonin has also been shown to benefit individuals suffering from insomnia (Hughes R J, Sack R L, Lewy A J. The role of melatonin and circadian phase in age-related sleep-maintenance insomnia: assessment in a clinical trial of melatonin replacement. Sleep. 1998; 21(1):52-68; Zhdanova I V, Wurtman R J, Regan M M, Taylor J A, Shi J P, Leclair O U. Melatonin treatment for age-related insomnia. J Clin Endocrinol Metab. 2001 October; 86(10):4727-30; Brzezinski A, Vangel M G, Wurtman R J, Norrie G, Zhdanova I, Ben-Shushan A, Ford I. Effects of exogenous melatonin on sleep: a meta-analysis. Sleep Med Rev. 2005 February; 9(1):41-50.) by way of the induction of sleep. The most common effect of melatonin on sleep is a reduction in sleep latency, the time taken to fall asleep (Zhdanova I V, Wurtman R J, Lynch H J, Ives J R, Dollins A B, Morabito C, Matheson J K, Schomer D L. Sleep-inducing effects of low doses of melatonin ingested in the evening. Clin Pharmacol Ther. 1995 May; 57(5):552-8; Nagtegaal J E, Kerkhof G A, Smits M G, Swart A C, Van Der Meer Y G. Delayed sleep phase syndrome: A placebo-controlled cross-over study on the effects of melatonin administered five hours before the individual dim light melatonin onset. J Sleep Res. 1998 June; 7(2):135-43; Kayumov L, Brown G, Jindal R, Buttoo K, Shapiro C M. A randomized, double-blind, placebo-controlled crossover study of the effect of exogenous melatonin on delayed sleep phase syndrome. Psychosom Med. 2001 January-February; 63(1):40-8; Buscemi N, Vandermeer B, Hooton N, Pandya R, Tjosvold L, Hartling L, Baker G, Klassen T P, Vohra S. The efficacy and safety of exogenous melatonin for primary sleep disorders. A meta-analysis. J Gen Intern Med. 2005 December; 20(12): 1151-8.), wherein it reduces the time it takes for an individual to fall asleep. Melatonin may also normalize the circadian rhythm and benefit shift workers and individuals with circadian rhythm disorders (Avery D, Lenz M, Landis C. Guidelines for prescribing melatonin. Ann Med. 1998 February; 30(1):122-30; Kunz D, Mahlberg R, Muller C, Tilmann A, Bes F. Melatonin in patients with reduced REM sleep duration: two randomized controlled trials. J Clin Endocrinol Metab. 2004 January; 89(1):128-34; Mundey K, Benloucif S, Harsanyi K, Dubocovich M L, Zee P C. Phase-dependent treatment of delayed sleep phase syndrome with melatonin. Sleep. 2005 Oct. 1; 28(10):1271-8.).

Melatonin may also been shown to be effective in treating seasonal depression (Lewy A J, Bauer V K, Cutler N L, Sack R L. Melatonin treatment of winter depression: a pilot study. Psychiatry Res. 1998 Jan. 16; 77(1):57-61.) and migraines (Peres M F, Zukerman E, da Cunha Tanuri F, Moreira F R; Cipolla-Neto J. Melatonin, 3 mg, is effective for migraine prevention. Neurology. 2004 Aug. 24; 63(4):757.). Furthermore, blood pressure as well as stress hormones can be reduced by daily oral administration of melatonin in healthy men (Arangino S, Cagnacci A, Angiolucci M, Vacca A M, Longu G, Volpe A, Melis G B. Effects of melatonin on vascular reactivity, catecholamine levels, and blood pressure in healthy men. Am J Cardiol. 1999 May 1; 83(9):1417-9.).

One aspect of the present invention includes the use of Melatonin for the regulation of sleep. U.S. Pat. Nos. 6,703, 412, 5,716,978, and 5,641,801 disclose methods of treating sleeplessness, sleep latency period, circadian rhythm disorders involving Melatonin.

For example, U.S. Pat. No. 6,703,412, entitled "Method of Treating Sleeplessness with Melatonin on an Acute Basis" purports to describe a method of treating sleeplessness in a human comprising the administration of an effective amount of not greater than 10 mg of melatonin or a pharmaceutically acceptable salt thereof. The method further comprises the administration of melatonin after a person has tried and failed to go to sleep, or has awakened from sleep and is unable to return to sleep. The method may be employed up to one hour from the person's desired waking time.

U.S. Pat. No. 5,716,978, entitled "Methods of Treating Circadian Rhythm Disorders" describes a method in which infants and blind humans employ the administration of Melatonin to produce a phase-shifting effect and reinstate a proper circadian rhythm. The method involves the administration of Melatonin from about 6 hours to about 19 hours prior to when a normal sleep phase should begin. The administration of Melatonin is to be less than 1 mg and at a time prior to a person's endogenous Melatonin onset time.

U.S. Pat. No. 5,641,801 entitled "Method of Reducing the Period before the Onset of Sleep" purports to describe a method of inducing sleep in an individual via the administration of a single dose of Melatonin comprising less than 1 mg to raise the peak plasma Melatonin levels to within physiological nocturnal levels of normal untreated individuals.

In an embodiment of the present invention, which is set forth in greater detail in Example 1 below, the supplemental composition may include Melatonin. A serving of the supplemental composition may include from about 0.001 g to about 0.01 g of Melatonin. The preferred dosage of a serving of the supplemental composition comprises about 0.0040 g of Melatonin.

Furthermore, in an embodiment of the present invention, which is set forth in greater detail in Example 1 below, the supplemental composition may include fine-milled Melatonin. A serving of the supplemental composition may include from about 0.0001 g to about 0.01 g of fine-milled Melatonin. The preferred dosage of a serving of the supplemental composition comprises about 0.0010 g of fine-milled Melatonin.

CoQ10

Coenzyme Q10 (CoQ10, ubiquinone) is found in the mitochondria of all cells and is involved in energy production. It is found at its highest concentrations in the heart, liver, kidney and pancreas. CoQ10 is a potent antioxidant in human blood (Weber C, Sejersgard Jakobsen T, Mortensen S A, Paulsen G, Holmer G. Antioxidative effect of dietary coenzyme Q10 in human blood plasma. Int J Vitam Nutr Res. 1994; 64(4):311-5.) where it also acts to preserve vitamin E, another major antioxidant (Thomas S R, Neuzil J, Stocker R. Inhibition of LDL oxidation by ubiquinol-10. A protective mechanism for coenzyme Q in atherogenesis? Mol Aspects Med. 1997; 18 Suppl:S85-103).

Due to its high concentrations in the heart, CoQ10 is believed to benefit and strengthen the heart. Many heart-related diseases are thought to result from defective myocardial energy production and numerous studies have suggested that supplementation with CoQ10 is beneficial (Mortensen S A. Perspectives on therapy of cardiovascular diseases with coenzyme Q10 (ubiquinone). Clin Investig. 1993; 71(8 Suppl):S116-23.). A meta-analysis of eight clinical trials supports the efficacy of CoQ10 for the treatment of congestive heart failure (Soja A M, Mortensen S A. Treatment of congestive heart failure with coenzyme Q10 illuminated by meta-analyses of clinical trials. Mol Aspects Med. 1997; 18 Suppl: S159-68.). Another study has shown that individuals suffering from angina were able to exercise for longer periods when receiving CoQ10 (Kamikawa T, Kobayashi A, Yamashita T, Hayashi H, Yamazaki N. Effects of coenzyme Q10 on exercise tolerance in chronic stable angina pectoris. Am J Cardiol. 1985 Aug. 1; 56(4):247-51.) as compared to untreated groups. Moreover, myocardial function was improved by CoQ10 in patients with disease conditions known to involve energy production deficits (Folkers K, Wolaniuk J, Simonsen R, Morishita M, Vadhanavikit S. Biochemical rationale and the cardiac response of patients with muscle disease to therapy with coenzyme Q10. Proc Natl Acad Sci USA. 1985 July; 82(13):4513-6.) wherein these patients also reported a 'subjective' improved sense of well being. CoQ10 supplemented with iron and vitamin B6 has also appeared to prevent the progression of Alzheimer's disease, a neurological disease often associated with impaired mitochondrial function (Imagawa M, Naruse S, Tsuji S, Fujioka A, Yamaguchi H. Coenzyme Q10, iron, and vitamin B6 in genetically-confirmed Alzheimer's disease. Lancet. 1992 Sep. 12; 340(8820):671.). Moreover, in another neurological disorder, CoQ10 in a phase II clinical trial was reported to slow the progression of Parkinson's disease (Shults C W, Oakes D, Kieburtz K, Beal M F, Haas R, Plumb S, Juncos J L, Nutt J, Shoulson I, Carter J, Kompoliti K, Perlmutter J S, Reich S, Stern M, Watts R L, Kurlan R, Molho E, Harrison M, Lew M; Parkinson Study Group. Effects of coenzyme Q10 in early Parkinson disease: evidence of slowing of the functional decline. Arch Neurol. 2002 October; 59(10):1541-50.) which often results in disturbed sleep and has been shown to involve impaired mitochondrial function and low levels of CoQ10 (Shults C W, Haas R H, Passov D, Beal M F. Coenzyme Q10 levels correlate with the activities of complexes I and II/III in mitochondria from parkinsonian and nonparkinsonian subjects. Ann Neurol. 1997 August; 42(2):261-4.).

Furthermore, CoQ10 has been successfully used to treat high blood pressure, eliminating the need for medication in many cases (Langsjoen P, Langsjoen P, Willis R, Folkers K. Treatment of essential hypertension with coenzyme Q10. Mol Aspects Med. 1994; 15 Suppl:S265-72.). Migraines have also been successfully and safely treated with CoQ10 (Sandor P S, Di Clemente L, Coppola G, Saenger U, Fumal A, Magis D, Seidel L, Agosti R M, Schoenen J. Efficacy of coenzyme Q10 in migraine prophylaxis: a randomized controlled trial. Neurology. 2005 Feb. 22; 64(4):713-5.) most likely due its effects on blood pressure.

In a Japanese study, CoQ10 was shown to provide relieve from snoring in about half of the subjects, displaying a decrease in the sound level of their snoring (Takasaki Y, Yoshida H, Kaneko Y, Kaneda R, Kurosaki S, Yamadera Y., An Analysis of Effectiveness of Activated Co-enzyme Q10 on Subjects by Using Acoustic Technology. Biopharma Ltd. Tokyo Japan). Specifically, about 44% of subjects displayed a decrease in the sound level of their snoring during the REM stage of sleep, about 40% of subjects showed a decrease in the sound level of their snoring during non-REM sleep stages I/II, and about 33% of subjects showed a decrease in the sound level of their snoring during non-REM sleep stages III/IV. Furthermore, subjects reported in questionnaires that their feeling of restfulness was improved upon waking.

In an embodiment of the present invention, which is set forth in greater detail in Example 1 below, the supplemental composition may include CoEnzyme Q10. A serving of the supplemental composition may include from about 0.0005 g to about 0.1000 g of CoEnzyme Q10. The preferred dosage of a serving of the supplemental composition comprises about 0.0010 g of CoEnzyme Q10.

Lemon Balm Leaf Extract

The plant *Melissa officinalis*, commonly known as Lemon balm is a member of the mint family and is often referred to as "the calming herb". Lemon balm extract has proven antioxidant activity which likely contributes to its beneficial effects (Hohmann J, Zupko I, Redei D, Csanyi M, Falkay G, Mathe I, Janicsak G. Protective effects of the aerial parts of Salvia officinalis, *Melissa Officinalis* and *Lavandula angustifolia* and their constituents against enzyme-dependent and enzyme-independent lipid peroxidation. Planta Med. 1999 August; 65(6):576-8.). However, in the central nervous system, it possesses acetylcholine receptor activity (Wake G, Court J, Pickering A, Lewis R, Wilkins R, Perry E. acetylcholine receptor activity in European medicinal plants traditionally used to improve failing memory. J Ethnopharmacol. 2000 February; 69(2):105-14.), therefore suggesting that it may have another possible mechanism of action relating to cell-signaling.

Randomized, placebo-controlled, double-blind clinical studies investigating the acute effects of Lemon balm extract on cognition and mood have demonstrated a calming effect (Kennedy D O, Scholey A B, Tildesley N T, Perry E K, Wesnes K A. Modulation of mood and cognitive performance following acute administration of *Melissa officinalis* (lemon balm). Pharmacol Biochem Behav. 2002 July; 72(4):953-64.) in addition to the effect of improved mood (Kennedy D O, Wake G, Savelev S, Tildesley N T, Perry E K, Wesnes K A, Scholey A B. Modulation of mood and cognitive performance following acute administration of single doses of *Melissa officinalis* (Lemon balm) with human CNS nicotinic and muscarinic receptor-binding properties. Neuropsychopharmacology. 2003 October; 28(10):1871-81.). Lemon balm extract has also shown potential in reducing the negative mood effects of stress in clinical trials (Kennedy D O, Little W, Scholey A B. Attenuation of laboratory-induced stress in humans after acute administration of *Melissa officinalis* (Lemon Balm). Psychosom Med. 2004 July-August; 66(4): 607-13.).

Moreover, the cognitive function of Alzheimer's patients has been shown to be improved by the use Lemon balm extract (Akhondzadeh S, Noroozian M, Mohammadi M, Ohadinia S, Jamshidi A H, Khani M. *Melissa officinalis* extract in the treatment of patients with mild to moderate Alzheimer's disease: a double blind, randomised, placebo controlled trial. J Neurol Neurosurg Psychiatry. 2003 July; 74(7):863-6.). In this study, the treatment group also displayed less agitation than the placebo group, suggesting an improvement in mood. Furthermore, clinical trials have demonstrated that Lemon balm can be effective at reducing stress and anxiety when used in combination with *Valeriana* (Kennedy D O, Little W, Haskell C F, Scholey A B. Anxiolytic effects of a combination of *Melissa officinalis* and *Valeriana officinalis* during laboratory induced stress. Phytother Res. 2006 February; 20(2):96-102.). Another study has shown that when presented in a lozenge also containing Lavender oil and hops, Lemon balm can alter brain-waves related to working memory, leading to the induction of a state of relaxation and an improved ability to cope with emotional and physiological stress (Dimpfel W, Pischel I, Lehnfeld R. Effects of lozenge containing lavender oil, extracts from hops, lemon balm and oat on electrical brain activity of volunteers. Eur J Med Res. 2004 Sep. 29; 9(9):423-31.).

In an embodiment of the present invention, which is set forth in greater detail in Example 1 below, the supplemental composition may include Lemon Balm leaf extract. A serving of the supplemental composition may include from about 0.0010 g to about 0.1000 g of Lemon Balm leaf extract. The preferred dosage of a serving of the supplemental composition comprises about 0.0800 g of Lemon Balm leaf extract.

Hops Cone Extract (*Humulus lupulus*)

The hop plant (*Humulus lupulus*) is a flowering vine used traditionally as a sedative to assist with anxiety reduction and sleep difficulties. In mice, hops extract displays sleep-enhancing and antidepressant activities (Zanoli P, Rivasi M, Zavatti M, Brusiani F, Baraldi M. New insight in the neuropharmacological activity of *Humulus lupulus* L. J Ethnopharmacol. 2005 Oct. 31; 102(1):102-6.).

In vitro tests have shown that hops contain compounds with antioxidant and chemoprotective activity as well as compounds that can induce detoxification enzymes (Dietz B M, Kang Y H, Liu G, Eggler A L, Yao P, Chadwick L R, Pauli G F, Farnsworth N R, Mesecar A D, van Breemen R B, Bolton J L. Xanthohumol isolated from *Humulus lupulus* Inhibits menadione-induced DNA damage through induction of quinone reductase. Chem Res Toxicol. 2005 August; 18(8): 1296-305.).

A combination of valerian and hops has been shown to interact with adenosine receptors (Muller C E, Schumacher B, Brattstrom A, Abourashed E A, Koetter U. Interactions of valerian extracts and a fixed valerian-hop extract combination with adenosine receptors. Life Sci. 2002 Sep. 6; 71(16):1939-49.) to aid in the maintenance of sleep. Moreover, binding of the valerian-hop combination to melatonin and serotonin receptors has also been shown (Abourashed E A, Koetter U, Brattstrom A. In vitro binding experiments with a Valerian, hops and their fixed combination extract (Ze91019) to selected central nervous system receptors. Phytomedicine. 2004 November; 11(7-8):633-8.). These two receptor types are also known to be involved in the sleep process. Furthermore, hop extract has been shown to modulate the gamma-aminobutyric acid receptor (GABA(A) receptors) and display GABA-like activity (Aoshima H, Takeda K, Okita Y, Hossain S J, Koda H, Kiso Y. Effects of beer and hop on ionotropic gamma-aminobutyric acid receptors. J Agric Food Chem. 2006 Apr. 5; 54(7):2514-9.) relating to sleep. GABA is an inhibitory neurotransmitter that can induce relaxation and sleep. Modulation of any or all of these receptors may mediate the sleep-inducing activity of hops.

Most of the studies examining the efficacy of hops to aid sleep employ hops in combination with other compounds acting on various receptors known to be involved in sleep regulation. A combination of valerian and hops has been shown to reduce the time taken to fall asleep and results in a more refreshed feeling in the morning in subjects suffering from mild to moderate insomnia (Fussel A, Wolf A, Brattstrom A. Effect of a fixed valerian-Hop extract combination (Ze 91019) on sleep polygraphy in patients with non-organic insomnia: a pilot study. Eur J Med Res. 2000 Sep. 18; 5(9):385-90.).

In an embodiment of the present invention, which is set forth in greater detail in Example 1 below, the supplemental composition may include Hops cone extract. A serving of the supplemental composition may include from about 0.0010 g to about 0.1000 g of Hops cone extract. The preferred dosage of a serving of the supplemental composition comprises about 0.0200 g of Hops cone extract.

Lavender Flower (*Lavandula officinalis*)

Oil from *Lavandula officinalis*, commonly known as the Lavender plant is frequently used in aromatherapy as a mode to induce relaxation. The mild sedative effects of Lavender have been demonstrated in animals and humans (Lis-Balchin M, Hart S. Studies on the mode of action of the essential oil of lavender (*Lavandula angustifolia* P. Miller). Phytother Res. 1999 September; 13(6):540-2.). Further to the sedative effect, Lavender oil has been shown to reduce agitation of patients suffering from dementia (Holmes C, Hopkins V, Hensford C, MacLaughlin V, Wilkinson D, Rosenvinge H. Lavender oil as a treatment for agitated behaviour in severe dementia: a placebo controlled study. Int J Geriatr Psychiatry. 2002 April; 17(4):305-8.). Moreover, Lavender has also been shown be beneficial for treating depression (Akhondzadeh S, Kashani L, Fotouhi A, Jarvandi S, Mobaseri M, Moin M, Khani M, Jamshidi A H, Baghalian K, Taghizadeh M. Comparison of *Lavandula angustifolia* Mill. tincture and imipramine in the treatment of mild to moderate depression: a double-blind, randomized trial. Prog Neuropsychopharmacol Biol Psychiatry. 2003 February; 27(1):123-7.). Additionally, the sleep-inducing effects of other compounds may be increased by Lavender (Gyllenhaal C, Merritt S L, Peterson S D, Block K I, Gochenour T. Efficacy and safety of herbal stimulants and sedatives in sleep disorders. Sleep Med Rev. 2000 June; 4(3): 229-251.).

U.S. Pat. No. 5,958,462, entitled "Therapeutic Bath Salts and Method of Use," describes a composition comprising magnesium, carbonate and copper compounds and optionally essential oils including that of Lavender. The composition comprises bath salts purported to be helpful in the relaxation of muscles, elimination or reduction of muscle spasms, and the overall enhancement of a person's mood when used as an aromatherapy.

In an embodiment of the present invention, which is set forth in greater detail in Example 1 below, the supplemental composition may include Lavender Flower powder. A serving of the supplemental composition may include from about 0.0010 g to about 0.0100 g of Lavender Flower powder. The preferred dosage of a serving of the supplemental composition comprises about 0.0050 g of Lavender Flower powder.

Passion Flower Extract

Passion flower has been used traditionally for relaxation and as a sleep-aid as well as a treatment for anxiety. The main active component of Passionflower is thought to by chrysin, one of several flavonoids which have been isolated from this plant (Menghini A, Mancini L A. TLC determination of flavonoid accumulation in clonal populations of *Passiflora incarnata* L. Pharmacol Res Commun. 1988 December; 20 Suppl 5:113-6; Pereira C A, Yariwake J H, Lancas F M, Wauters J N, Tits M, Angenot L. A HPTLC densitometric determination of flavonoids from *Passiflora alata, P. edulis, P. incarnata* and *P. caerulea* and comparison with HPLC method. Phytochem Anal. 2004 July-August; 15(4):241-8.). In mice, chrysin has been shown to act as an agonist of benzodiazepine receptors and also possess anti-anxiety activity (Wolfman C, Viola H, Paladini A, Dajas F, Medina J H. Possible anxiolytic effects of chrysin, a central benzodiazepine receptor ligand isolated from Passiflora coerulea. Pharmacol Biochem Behav. 1994 January; 47(1):1-4.). Studies have shown that, in mice, Passionflower extract reduces anxiety and induces sleep (Soulimani R, Younos C, Jarmouni S, Bousta D, Misslin R, Mortier F. Behavioural effects of *Passiflora incarnata* L. and its indole alkaloid and flavonoid derivatives and maltol in the mouse. J Ethnopharmacol. 1997 June; 57(1):11-20.). Clinical trials in humans have further demonstrated that Passionflower is effective in the treatment of anxiety (Akhondzadeh S, Naghavi H R, Vazirian M, Shayeganpour A, Rashidi H, Khani M. Passionflower in the treatment of generalized anxiety: a pilot double-blind randomized controlled trial with oxazepam. J Clin Pharm Ther. 2001 October; 26(5):363-7.).

One aspect of the present invention includes the use of Passionflower extract for the reduction of stress and anxiety. U.S. Pat. Nos. 6,080,410 and 5,681,578 describe a method and composition, respectively, employing Passionflower extracts for the reduction of stress and anxiety.

U.S. Pat. No. 6,080,410, entitled "Method for Reducing Daily Stress and Anxiety in Adults," describes a method of employing a novel dietary supplement which serves a general relaxant comprised of Kava root extract, and at least one of Passionflower, Chamomile Flower, Hops, and Schizandra Fruit. The method claims to reduce daily stress and anxiety in adults. It is administered in capsule format.

U.S. Pat. No. 5,681,578, entitled "Composition for Relieving Stress Anxiety, Grief, And Depression," describes a composition comprising gamma Aminobutyric acid, glutamine, glycine, magnesium, passionflower, primal officinalis and vitamin B6. The composition is purported to relieve stress, anxiety, grief and depression.

In an embodiment of the present invention, which is set forth in greater detail in Example 1 below, the supplemental composition may include Passionflower extract. A serving of the supplemental composition may include from about 0.0010 g to about 0.0100 g of Passionflower extract. The preferred dosage of a serving of the supplemental composition comprises about 0.0020 g of Passionflower extract.

Skullcap (*Scutellaria lateriflora*)

Scutellaria, also known commonly as Skullcap, is a member of the mint family and has been used traditionally to treat depression and stress. Studies in mice indicate that Skullcap reduces anxiety (Awad R, Arnason J T, Trudeau V, Bergeron C, Budzinski J W, Foster B C, Merali Z. Phytochemical and biological analysis of skullcap (*Scutellaria lateriflora* L.): a medicinal plant with anxiolytic properties. Phytomedicine. 2003 November; 10(8):640-9.). The effects of Skullcap may be at least partially mediated by antagonism of serotonin receptors (Gafner S, Bergeron C, Batcha L L, Reich J, Arnason J T, Burdette J E, Pezzuto J M, Angerhofer C K. Inhibition of [3H]-LSD binding to 5-HT7 receptors by flavonoids from *Scutellaria lateriflora*. J Nat Prod. 2003 April; 66(4):535-7.). A clinical study involving healthy volunteers also demonstrated that Skullcap reduces anxiety (Wolfson P, Hoffmann D L. An investigation into the efficacy of *Scutellaria lateriflora* in healthy volunteers. Altern Ther Health Med. 2003 March-April; 9(2):74-8.).

U.S. Pat. No. 7,045,158, entitled "Standardized Extracts of *Scutellaria Laterifloa*," describes an improved extract of *Scutellaria Laterifloa* and relates to a pharmaceutical composition prepared from said extract wherein it is suitable for treating anxiety, insomnia, convulsions, muscle tension and spasms.

In an embodiment of the present invention, which is set forth in greater detail in Example 1 below, the supplemental composition may include Skullcap powder. A serving of the supplemental composition may include from about 0.0001 g to about 0.0100 g of Skullcap powder. The preferred dosage of a serving of the supplemental composition comprises about 0.0010 g of Skullcap powder.

Valerian Root (*Valeriana officinalis*)

*Valeriana officinalis*, wherein the root, normally called Valerian root, is a perennial herb traditionally used as a sedative and sleep-aid. Compounds from Valerian interact with GABA, melatonin, and/or adenosine systems through binding to certain melatonin and serotonin receptor subtypes (Abourashed E A, Koetter U, Braftstrom A. In vitro binding experiments with a Valerian, hops and their fixed combination extract (Ze91019) to selected central nervous system receptors. Phytomedicine. 2004 November; 11(7-8):633-8.), particularly the $5\text{-HT}_{5A}$ subtype (Dietz B M, Mahady G B, Pauli G F, Farnsworth N R. Valerian extract and valerenic acid are partial agonists of the 5-HT5a receptor in vitro. Brain Res Mol Brain Res. 2005 Aug. 18; 138(2):191-7.). Interaction with this receptor is thought to be responsible for the sleep-inducing and maintenance effect of Valerian root extract.

Valerian root extract has proven to be useful in several clinical trials. Subjective self-evaluation of sleep quality improved in a valerian supplemented group as part of a randomized controlled trial (Leathwood P D, Chauffard F, Heck E, Munoz-Box R. Aqueous extract of valerian root (*Valeriana officinalis* L.) improves sleep quality in man. Pharmacol Biochem Behav. 1982 July; 17(1):65-71.), compared to control groups. In another clinical trial, the valerian group reported improved sleep over the placebo group, with 89% of participants reporting improved sleep (Lindahl O, Lindwall L. Double blind study of a valerian preparation. Pharmacol Biochem Behav. 1989 April; 32(4):1065-6.). Sleep was additionally improved in children with various intellectual deficits, particularly those with hyperactivity (Francis A J, Dempster R J. Effect of valerian, *Valeriana edulis*, on sleep difficulties in children with intellectual deficits: randomised trial. Phytomedicine. 2002 May; 9(4):273-9.).

One aspect of the present invention includes the use of Valerian for improving the quality of sleep and reducing minor aches and pains. U.S. Pat. Nos. 6,869,622 and 6,383,527 describe respective compositions for improving the quality of sleep and alleviating muscular aches and strains, particularly with respect to those in the lower back.

For example, U.S. Pat. No. 6,869,622, entitled "Composition for Improving Sleep Quality and Efficiency, And Method of Preparing and Using the Composition," describes a pharmaceutically active extract of the plant root family of Valerianaceae and its usefulness in improving sleep quality and efficiency. The patent purports to relate to a method for reducing the number of times a patient wakes after sleep onset, comprising administering to the patient a pharmaceutically-active extract of the root of a plant of the family Valerianaceae, wherein it is processed via an ethanolic and water extraction. Furthermore, a single dosage is administered between the range of 50 mg and 5000 mg approximately one-half and two hours prior to bedtime.

U.S. Pat. No. 6,383,527, entitled "Compositions Comprising Valerian Extracts, Isovaleric Acid or Derivatives Thereof with a NSAID," purports to describe a combination of valerian extract or isovaleric acid or a derivative in with a non-steroidal anti-inflammatory compound for treating acute muscular aches, strains and sprains, and in particular lower back pain.

In an embodiment of the present invention, which is set forth in greater detail in Example 1 below, the supplemental composition may include Valerian Root. A serving of the supplemental composition may include from about 0.1000 g to about 1.000 g of Valerian Root. The preferred dosage of a serving of the supplemental composition comprises about 0.1200 g of Valerian Root.

Willow Bark Extract (Providing Salicin) (*Salix alba*) 25% Salicin

Willow bark (*Salix alba*) is a source of salicin, a precursor of acetylsalicylic acid (aspirin) traditionally used to treat pain, fever and inflammation. In a blind clinical trial, willow bark was demonstrated to be effective at relieving back pain (Chrubasik S, Eisenberg E, Balan E, Weinberger T, Luzzati R, Conradt C. Treatment of low back pain exacerbations with willow bark extract: a randomized double-blind study. Am J Med. 2000 July; 109(1):9-14.). After four weeks, 39% of the high salicin group (n=65) were pain-free, 21% of the low salicin group (n=67) were pain-free, and only 6% of the placebo group (n=59) were pain-free. Willow bark extract has also been shown to effectively reduce arthritis pain (Schmid B, Ludtke R, Selbmann H K, Kotter I, Tschirdewahn B, Schaffner W, Heide L. Efficacy and tolerability of a standardized willow bark extract in patients with osteoarthritis: randomized placebo-controlled, double blind clinical trial. Phytother Res. 2001 June; 15(4):344-50.).

The diminishment of bodily pain is an integral part of quality sleep. The inclusion of Willow Back Extract aids in the alleviation of minor bodily pains, leading to an improvement in sleep quality and a reduction in sleep disruption due to discomfort.

One aspect of the present invention includes the use of Willow bark for the attenuation of minor aches and pains, leading to an improved quality of sleep. U.S. Pat. Nos. 6,770,263 and 6,312,736 describe compositions for the treatment, e.g., alleviation, of aches and pains.

For example, U.S. Pat. No. 6,770,263, entitled "Compositions and Methods for the Treatment of Aches and Pains," purports to describe methods and compositions useful for treating aches and/or pains. The composition comprises an aqueous medium having dispersed or dissolved therein an analgesic selected from the group consisting of white willow bark, aspirin; ibuprofen, naproxen, and any combination thereof. The composition is then administered in an effective amount across a mucosal membrane.

U.S. Pat. No. 6,312,736, entitled "Herbal Composition to Relieve Pain," describes a composition used to relieve pain and other symptoms associated with migraines and other types of headaches. The composition comprises a combination of White Willow bark extract, Kava Kava root extract, Feverfew extract, Ginger root extract, Guarana extract, and Vitamin B6 wherein the composition may be combined with liposomes to carry the composition in a sublingual dosage for fast pain relief.

In an embodiment of the present invention, which is set forth in greater detail in Example 1 below, the supplemental composition may include Willow bark extract. A serving of the supplemental composition may include from about 0.1000 g to about 1.000 g of Willow bark extract. The preferred dosage of a serving of the supplemental composition comprises about 0.1500 g Willow bark extract.

The present invention, according to an embodiment thereof, provides a method which includes the step of consuming a composition, wherein the method may, for example, alleviate minor aches and pains, speedily induce sleep, as well as provide for maintenance of sleep thereby promoting a good quality, restful sleep. In an embodiment of the present invention, the method includes the daily consumption, prior to going to sleep with the intent of a full night's sleep, of a sleep-promoting and pain-relief composition that may include at least an extract of Valerian Root, an extract of Willow Bark and Melatonin or a derivative thereof. Furthermore, the sleep-promoting and pain-relief composition may further comprise Coenzyme Q10, Lemon Balm leaf extract, Hops cone extract, Lavender flower extract, Passionflower extract, and Skullcap powder.

The present supplemental composition, or those similarly envisioned by one of skill in the art, may be utilized in methods to alleviate minor aches and pains, speedily induce sleep, as well as provide for maintenance of sleep thereby promoting a good quality, restful sleep in a formulation designed to be consumed on a daily basis prior to going to sleep with the intent of a night's rest.

In an embodiment of the present invention, the composition may include a time-release mechanism, e.g., wherein the time-release mechanism provides 4 hours of active compound release. Also, in various embodiments, the melatonin may be incorporated into a tablet coating to promote sleep more quickly, e.g., to promote instant or immediate sleep.

Although the following example illustrates the practice of the present invention one of its embodiments the example should not be interpreted as limiting the scope of the invention. Other embodiments of the present invention will be apparent to those of skill in the art form consideration of the specification and example.

EXAMPLE 1

A supplemental composition is provided on a daily basis, prior to going to sleep with the intent on a full night's rest, the composition utilizing a dual-release caplet formulation comprising Melatonin (0.0040 g), fine-milled Melatonin (0.0010 g), Coenzyme Q10 (0.0010 g), Hops cone extract (0.0200 g), Lavender flower powder (0.0050 g), Passionflower extract (0.0020 g), Skullcap powder (0.0010 g), Lemon Balm leaf extract (0.0800 g), deodorized Valerian root (0.1200 g) and Willow bark extract (0.1500 g).

Directions: As a supplemental composition, 1 caplet is orally administered with an 8 oz. glass of water once daily prior to going to sleep. Preferably, the supplemental composition is consumed with the intent of a full night's sleep.

What is claimed:

1. A method for promoting sleep, the method comprising orally administering to a human or animal a composition consisting essentially of:

an extract of Valerian Root;
an extract of Willow Bark;
Melatonin;
an extract of Hops cone;
Lavender flower powder;
an extract of Passionflower;
Skullcap powder;
Coenzyme Q10; and
an extract of Lemon Balm.

2. The method of claim 1, wherein promoting sleep includes at least one of inducing sleep and maintaining sleep.

3. The method of claim 1, wherein the composition is administered to a user once daily prior to the user going to sleep.

4. The method of claim 1, wherein the composition comprises a time-release mechanism providing about 4 hours of active compound release.

5. The method of claim 1, wherein composition is provided in the form of a coated tablet, and the melatonin is incorporated into the tablet coating.

6. The method of claim 1, wherein at least a portion of the melatonin is fine-milled.

* * * * *

UNITED STATES PATENT AND TRADEMARK OFFICE
CERTIFICATE OF CORRECTION

| | | |
|---|---|---|
| PATENT NO. | : 7,476,405 B2 | |
| APPLICATION NO. | : 11/486866 | |
| DATED | : January 13, 2009 | |
| INVENTOR(S) | : Heuer et al. | |

It is certified that error appears in the above-identified patent and that said Letters Patent is hereby corrected as shown below:

ON TITLE PAGE [12]

"Gardiner et al." should read --Heuer et al.--.

ON TITLE PAGE [75] INVENTORS

Inventors, "Paul T. Gardiner, Mississauga, (CA);" should be deleted; and "Kenneth Clement, Mississauge, (CA)" should read --Kenneth Clement, Mississauga, (CA)--.

ON TITLE PAGE [56] REFERENCES CITED

Other Publications, (after Strecker et al.) "basal forebrain and" (second occurrence) should be deleted; (after Zanoli, P. et al.) "Oct. 31, 2005; 102-6." should read --Oct. 31, 2005; 102(1):102-6.--; and (after Zeitzer et al.) "brain sleep" should read --brain during sleep--.

ON TITLE PAGE [57] ABSTRACT

Line 5, "person" should read --person's--.

COLUMN 1

Line 22, "well being" should read --well-being--.

COLUMN 3

Line 16, "levels Portas C M," should read --levels (Portas C M,--; and
Line 57, "a animal" should read --an animal--.

COLUMN 4

Line 34, "timed release" should read --timed-release--; and
Line 59, "test" should read --tests--.

COLUMN 8

Line 4, "well" should read --well--; and
Line 38, "relieve" should read --relief--.

UNITED STATES PATENT AND TRADEMARK OFFICE
CERTIFICATE OF CORRECTION

PATENT NO. : 7,476,405 B2
APPLICATION NO. : 11/486866
DATED : January 13, 2009
INVENTOR(S) : Heuer et al.

It is certified that error appears in the above-identified patent and that said Letters Patent is hereby corrected as shown below:

COLUMN 10

Line 67, "shown be" should read --shown to be--.

COLUMN 11

Line 28, "Passion Flower" should read --Passion flower--.

COLUMN 12

Line 39, "*Scutellaria Laterifloa*,"" should read --*Scutellaria Lateriflora*,"--;
Line 40, "*Scutellaria Laterifloa*" should read --*Scutellaria Lateriflora*--; and
Line 58, "Braftstrom A." should read --Brattstrom A.--.

COLUMN 15

Line 2, "invention one" should read --invention in one--; and
Line 5, "form" should read --from--.

COLUMN 16

Line 19, "composition" should read --the composition--.

Signed and Sealed this

Sixteenth Day of June, 2009

JOHN DOLL
*Acting Director of the United States Patent and Trademark Office*